United States Patent
Muijs Van De Moer et al.

(10) Patent No.: US 7,169,168 B2
(45) Date of Patent: Jan. 30, 2007

(54) SEALING DEVICE

(75) Inventors: Wouter Matthijs Muijs Van De Moer, Rotterdam (NL); Rienk Rienks, AN Putten (NL)

(73) Assignee: Kensey Nash Corporation, Exton, PA (US)

( * ) Notice: Subject to any disclaimer, the term of this patent is extended or adjusted under 35 U.S.C. 154(b) by 451 days.

(21) Appl. No.: 10/645,409

(22) Filed: Aug. 21, 2003

(65) Prior Publication Data

US 2004/0098044 A1    May 20, 2004

Related U.S. Application Data

(63) Continuation of application No. 09/617,286, filed on Jul. 17, 2000, now Pat. No. 6,764,500, which is a continuation of application No. 08/837,965, filed on Apr. 14, 1997, now Pat. No. 6,190,400, which is a continuation of application No. 08/369,264, filed on Jan. 5, 1995, now Pat. No. 5,620,461, which is a continuation of application No. 08/187,788, filed on Jan. 26, 1994, now abandoned, which is a continuation of application No. 07/781,091, filed on Oct. 22, 1991, now abandoned.

(30) Foreign Application Priority Data

May 29, 1989  (NL) ..................... 8901350
May 29, 1990  (WO) ..................... PCT/NL90/00078

(51) Int. Cl.
*A61B 17/08* (2006.01)

(52) U.S. Cl. ............ 606/213; 606/215; 606/232

(58) Field of Classification Search ........ 606/213, 606/215, 220, 232, 139, 144, 148, 157, 108; 128/898

See application file for complete search history.

(56) References Cited

U.S. PATENT DOCUMENTS

| | | | |
|---|---|---|---|
| 2,934,068 A | 4/1960 | Graham, Jr. et al. |
| 3,447,533 A | 6/1969 | Spicer |
| 3,538,917 A | 11/1970 | Selker |
| 3,675,639 A | 7/1972 | Cimber |
| 3,874,388 A | 4/1975 | King et al. |
| 4,007,743 A | 2/1977 | Blake |
| 4,168,708 A | 9/1979 | Lepley, Jr. et al. |
| 4,263,917 A | 4/1981 | Moss |
| 4,365,621 A | 12/1982 | Brundin |
| 4,390,018 A | 6/1983 | Zubrowski |
| 4,512,342 A | 4/1985 | Zaneveld et al. |
| 4,519,392 A | 5/1985 | Lingua |

(Continued)

FOREIGN PATENT DOCUMENTS

EP    0298533 A1    1/1989

(Continued)

*Primary Examiner*—Julian W. Woo
(74) *Attorney, Agent, or Firm*—Caesar, Rivise, Bernstein, Cohen & Pokotilow, Ltd.

(57) ABSTRACT

A percutaneously insertable system for sealing punctures in blood vessels includes an element that is percutaneously insertable into and deplorable within a blood vessel, a thread-like member attached to the element that passes through the wall of the blood vessel and arresting element movable on the thread and into engagement with the other surface of the blood vessel thereby to seal the opening.

24 Claims, 4 Drawing Sheets

U.S. PATENT DOCUMENTS

| | | |
|---|---|---|
| 4,532,926 A | 8/1985 | O'Holla |
| 4,606,337 A | 8/1986 | Zimmermann et al. |
| 4,669,473 A | 6/1987 | Richards et al. |
| 4,705,040 A * | 11/1987 | Mueller et al. ............. 606/108 |
| 4,744,364 A | 5/1988 | Kensey |
| 4,749,689 A | 6/1988 | Miyata et al. |
| 4,750,492 A | 6/1988 | Jacobs |
| 4,836,204 A | 6/1989 | Landymore et al. |
| 4,890,612 A | 1/1990 | Kensey |
| 4,917,089 A | 4/1990 | Sideris |
| 4,935,028 A | 6/1990 | Drews |
| 5,021,059 A | 6/1991 | Kensey et al. |
| 5,053,046 A | 10/1991 | Janese |
| 5,061,274 A | 10/1991 | Kensey |
| 5,192,302 A | 3/1993 | Kensey et al. |
| 5,275,616 A | 1/1994 | Fowler |
| 5,282,827 A | 2/1994 | Kensey et al. |
| 5,306,254 A | 4/1994 | Nash et al. |
| 5,330,445 A | 7/1994 | Haoga |
| 5,342,393 A | 8/1994 | Stack |
| 5,350,399 A | 9/1994 | Erlebacher et al. |
| 5,354,271 A | 10/1994 | Voda |

FOREIGN PATENT DOCUMENTS

| | | |
|---|---|---|
| EP | 0482350 A2 | 4/1992 |
| SU | 1088709 | 4/1984 |

* cited by examiner

SEALING DEVICE

RELATED APPLICATIONS

This application is a continuation of application Ser. No. 09/617,286, filed Jul. 17, 2000 now U.S. Pat. No. 6,764,500, which is a continuation of application Ser. No. 08/837,965, filed Apr. 14, 1997, now U.S. Pat. No. 6,190,400, issued Feb. 20, 2001, which is a continuation of Ser. No.08/369,264, filed Jan. 5, 1995, now U.S. Pat. No. 5,620,461, issued Apr. 15, 1997, which is a continuation of application Ser. No. 08/187,788, filed Jan. 26, 1994 now abandoned, which is a continuation of application Ser. No. 07/781,091, filed Oct. 22, 1991 now abandoned.

BACKGROUND OF THE INVENTION

The invention is concerned with a sealing device for the closure of puncture holes in blood vessels.

In the case of invasive investigations and intervention in medical practice, it is necessary that access be gained to the system of blood vessels in question (arterial or venous). This can take place surgically by direct vision or by way of percutaneous puncture whereby the blood vessel must first be located "blind" with a hollow needle (so-called feeling with the needle). After feeling with the needle, a tracer is then inserted through the needle into the blood vessel. When the positioning of the tracer has been verified, the needle is removed over the tracer. Next, a dilator is pushed in over the tracer with the objective of making the puncture opening large enough to position a so-called "sheath" or "introducer" in the blood vessel. This sheath consists of a hollow tube made of plastic whereby one extremity, which is open, is pushed up into the blood vessel and the other extremity, which is sealed by a so-called "hemostatic valve", is left outside the body. The hemostatic valve is made of rubber and is designed in such a way that objects (in particular, tracers and catheters) can be inserted through it into the sheath and can then be withdrawn again through it without this leading to blood being lost out of the sheath. The dilator is removed after the sheath has been inserted into the blood vessel by passing it over the dilator. In this way, an access route to the blood vessel remains open through which tracers, catheters etc. can be inserted with ease. The sheath is removed from the blood vessel after the procedure is finished. As a result, an opening remains in the blood vessel (the so-called puncture site) through which blood can flow to the outside (bleeding). In order to stanch bleeding from the puncture site, the blood vessel must be closed by applying pressure (pressing) in order to allow time for the blood clotting mechanism to form a clot at the puncture site. Depending on whether the patient has had larger or smaller amounts of anti-clotting agents (anticoagulants), the time over which pressure has to be applied varies, in the case of an arterial puncture, from 15 minutes to more than an hour. Once the bleeding has stopped, an elastic bandage (pressure bandage) is placed over the site of the puncture; this exerts pressure to as to prevent the blood clot from being washed away by the pressure in the blood vessel which can easily happen, especially in the case of an arterial puncture. This pressure bandage must remain in place for some time, varying from clinic to clinic from 8 to 24 hours. During the period of time that the pressure bandage is in place, the patient must remain resting in bed. After removing the pressure bandage, the patient can become mobile again. After an intra-arterial examination, this usually means, in practice, that the patient must stay in the hospital overnight and then go home the following morning.

The procedure is associated with quite a few complications which are inherent in the technique which is currently used. Thus intense bleeding can occur in addition to aneurysms (outward swellings of the wall of the blood vessel at the site of the puncture) and pseudo-aneurysms (whereby a passage exists, via the puncture site, between the lumen of the blood vessel and a clot situated around the blood vessel (hematoma). Arteriovenous fistulas (passages between the arterial and venous systems of blood vessels) can also arise. Neighboring nerves can also become pinched if bleeding is sufficiently profuse, resulting in pain, sensation disturbances or even paralysis of the groups of muscles which are innervated by these nerves. These complications arise in approximately 1% of all procedures. Surgical intervention is sometimes necessary whereby the hematoma is relieved and puncture site is sutured over (and, if required, any fistula is sealed).

SUMMARY OF THE INVENTION

In accordance with the invention, a means is envisaged to provide immediate closure of the puncture site by means of a sealing device which is introduced into the blood vessel through a sheath. This sealing device must be of such a form that it lies in the puncture site in a stable manner, does not seal the lumen of the blood vessel, does not cause intraluminal thrombi and decomposes after a certain period of time without causing emboli to form. In addition, repeated puncture of the same segment of the blood vessel must remain a possibility and there must be no allergic reactions to the material used. Of course, the material used must also be non-toxic and must be biocompatible.

This objective is achieved in accordance with the invention by means of a sealing device for the closure of openings in blood vessels which comprises an element that is capable of unfolding, which is introduced into the blood vessel, together with a fixation attachment connected to it. In this way, the element which is capable of unfolding can even serve as a sealing element if it is constructed in the form of a flexible sheet. However, it is also possible to use a tubular element as the sealing device that is pushed into the blood vessel. In addition, it is possible to construct the sealing element in the form of an inflatable element. The fixation attachment preferably consists of a thread. In the event that a flexible sheet is used as the sealing element which is introduced into the blood stream, then, in accordance with a preferred embodiment of the invention, an arresting element is applied over the fixation attachment on the outside of the blood vessel.

The elements and/or the fixation attachment in accordance with the invention preferably consist of bioresorbable material. An example of this is collagen. In the event that the fixation attachment comprises a fixation thread, the bioresorbable material is, for example, the same material that is used for surgical suturing thread, e.g., catgut or polyglactin.

The sealing device is also termed an occluder in the following specification.

In an embodiment of the occluder in accordance with the invention, the sealing element—also called a plug—is designed in such a way that it unfolds in the blood vessel after passing through the sheath and can, therefore, no longer come out again. In such an embodiment, the plug is preferably essentially circular, heart-shaped or oval. The fixation attachment or the fixation thread remains on the outside of the blood vessel in such an embodiment and is held in place by the skin. The fixation attachment is positioned through the site of the puncture. During removal of the sheath, the plug which has been inserted into the blood vessel is carefully pulled back toward the puncture site. The fixation attachment is preferably positioned essentially in the center of the flat sheet or in the vicinity thereof. The plug completely seals off the puncture site after the sheath has been removed. The fixation attachment can then be sutured to the skin.

In another embodiment, the sealing element is applied to the blood vessel from the outside and the element which is capable of unfolding is inserted into the blood vessel in order to provide a means of fastening the fixation attachment to which the sealing element is joined. In such an embodiment, it is not necessary that the element which is capable of unfolding has a flat, sheet-like form; on the contrary, it can take any form as long as satisfactory points of contact are provided on the inside of the blood vessel. In such a case, the sealing element can comprise a displaceable, tubular part which passes tightly over the fixation attachment and which is moved by the wall of the blood vessel. This type of arrangement can be effected by means of a tube or a small pipe.

The material of the plug, in particular collagen, causes a clot to form locally that is located in contact with the internal or external wall of the blood vessel; the material is completely resorbed during the course of time, usually over a period of several weeks.

Spontaneous resorption also takes place over a period of several weeks when using the preferred embodiment of the invention, i.e., a plug of collagen and a resorbable fixation attachment.

The invention is explained in more detail below by means of examples of embodiments which are reproduced in the drawings.

DETAILED DESCRIPTION OF THE PREFERRED EMBODIMENTS

Figure 1:
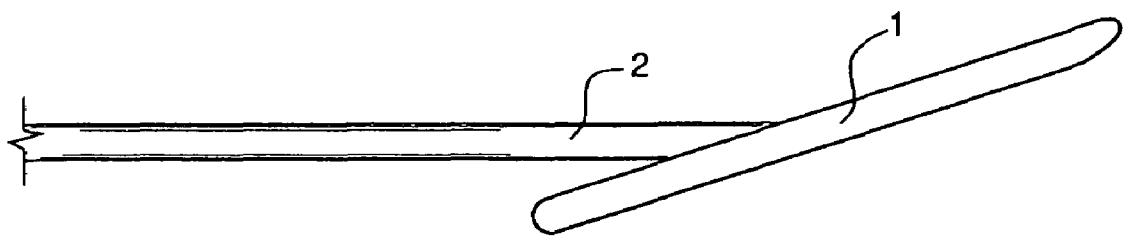
FIG. 1 shows a side view of a first embodiment of the sealing device in accordance with the invention.

A first embodiment of the sealing device in accordance with the invention is shown in the form of a side view in FIG. 1. This comprises a flexible sheet 1 as the sealing element and, in the center connected thereto, a fixation attachment 2, fashioned here in the form of a thread. The same arrangement is sketched in the form of a view from above in FIG. 2.

Figure 2:
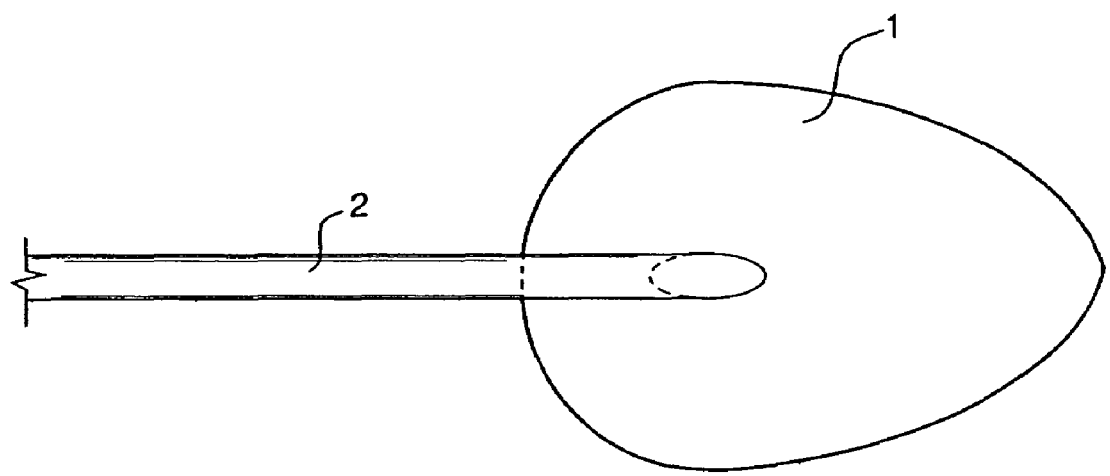
FIG. 2 shows the same embodiment seen from above.
Figure 4:
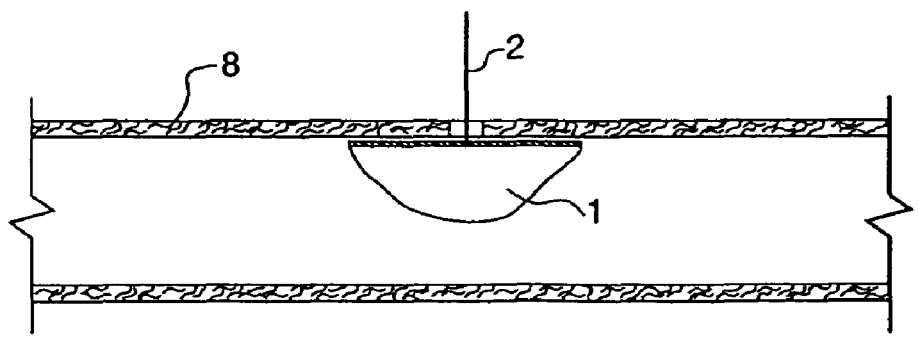
FIG. 4 shows the sealing device introduced into a blood vessel in accordance with the aforementioned embodiment.
Figure 3:
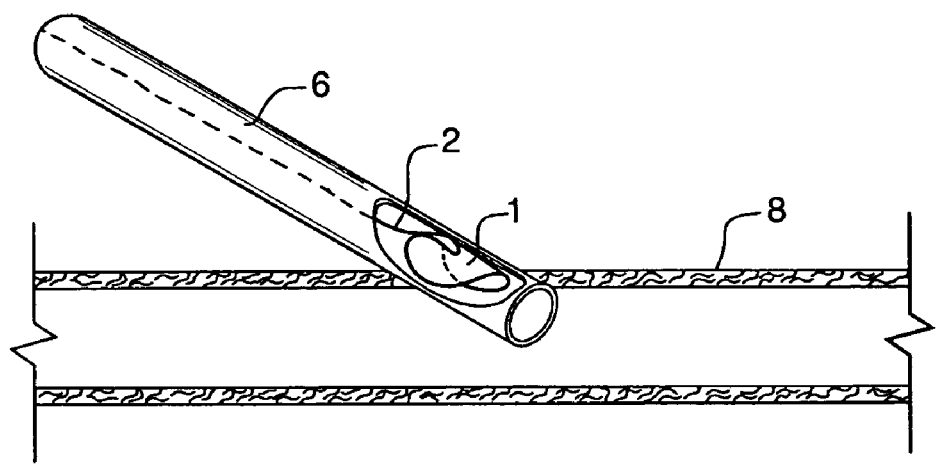
FIG. 3 shows the introduction of the sealing device into a blood vessel in accordance with FIG. 1 and 2.

A blood vessel 8 is illustrated in FIG. 3 in which a sheath 6 has been introduced as is carried out for various types of medical applications. After removing the sheath 6, the problem existed until now that a considerable opening arose in the blood vessel which had to be sealed in some way. The means described in the prior art for effecting such sealing have been found to be unreliable or to impose restrictions on the patient in terms of his or her movement. In accordance with the invention, the device portrayed in FIGS. 1 and 2 is inserted through the sheath as illustrated. After the sealing element 1 has been introduced into the blood vessel 8, the sheet 1 which is capable of unfolding unfolds in such a way that its surface area is greater than the surface area of the opening which is to be sealed. The sheath 6 is next moved out of the opening whereupon this will become somewhat smaller. By pulling on the fixation thread 2, sheet 1 will come into contact with the blood vessel 8 as illustrated in FIG. 4. By manufacturing both sheet 1 and the fixation attachment 2 from resorbable material, it is guaranteed that these parts will disappear (e.g., after a period of several weeks) after the opening in the blood vessel has been closed by healing.

Figure 5A:
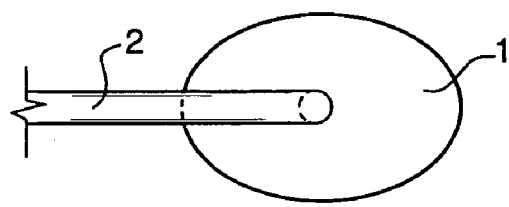
FIGS. 5*a, b* and *c* show a view from above of further embodiments of the sealing device in accordance with the invention.
Figure 5B:
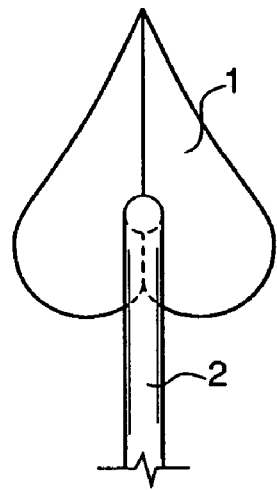
Figure 5C:
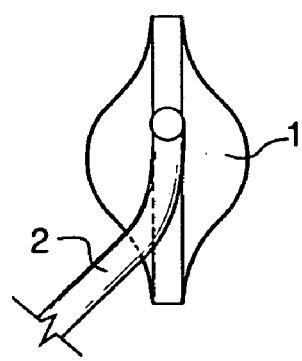

Various other embodiments of the flexible, sealing element or plug 1 are illustrated in FIGS. 5*a, b* and *c*. These can be used depending on the opening made in the blood vessel and depending on the particular possibilities available for inserting them through the sheath.

Figure 6:
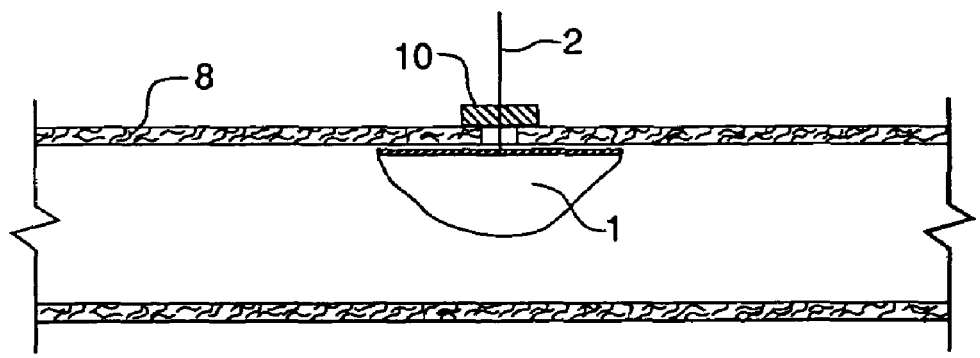
FIG. 6 shows a further embodiment of the sealing device introduced into a blood vessel in accordance with the invention.

FIG. 6 portrays a further embodiment of the sealing device in accordance with the invention. This is largely in conformity with the sealing device described by means of the above figures except that an arresting ring 10 is applied over the fixation thread 2. This arresting ring 10 serves to define the position of the sealing element 1 in a precise manner and is also manufactured from a biologically resorbable material. The ring 10 has an internal diameter such that, on the one hand, it can slide smoothly over the fixation attachment 2 but, on the other hand, it provides some degree of grip between the two parts.

Figure 7A:
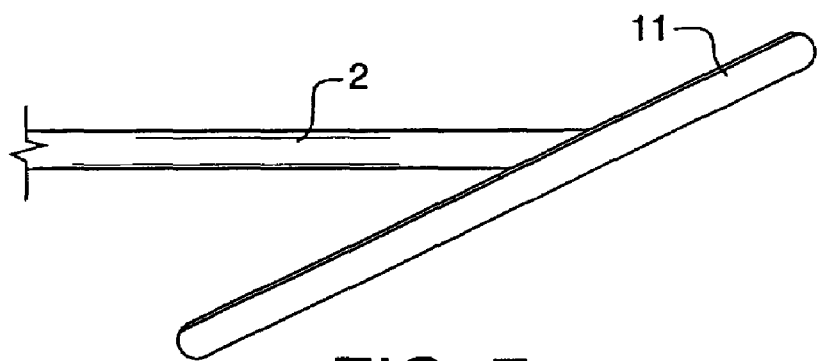
FIGS. 7*a, b* and *c* show parts of a further embodiment of the sealing device in accordance with the invention.
Figure 7B:
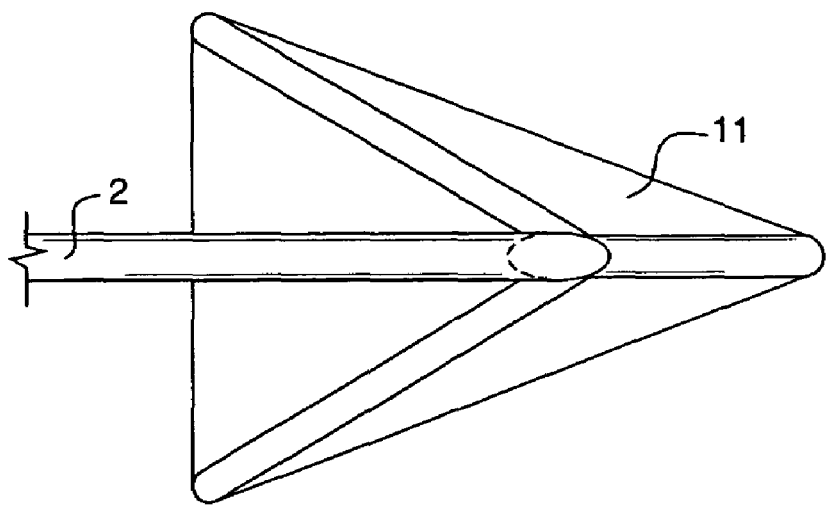
Figure 7C:
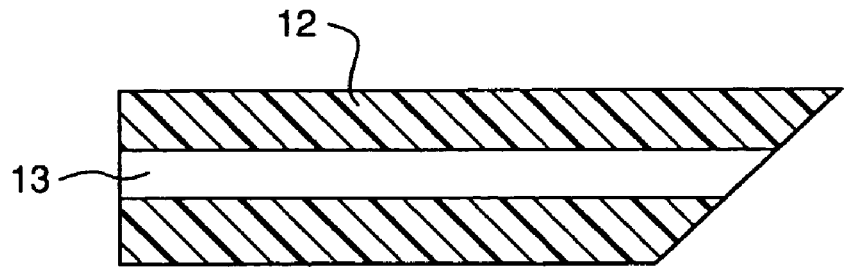
Figure 8:
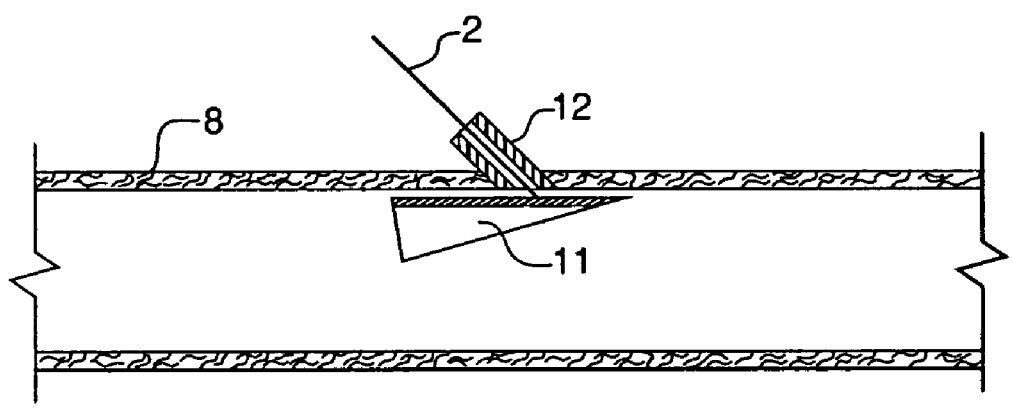
FIG. 8 shows the sealing device introduced into a blood vessel in accordance with FIG. 7.

FIGS. 7*a, b* and *c* show a further sealing device in accordance with the invention. The part joined to the fixation attachment is indicated by the number 11 in this embodiment. Just as in the preceding embodiments, part 11 is an element which is capable of unfolding that is to be introduced into the blood vessel but, in contrast to the previous embodiments, it does not serve as a sealing element. The chamfered tube indicated by the reference number 12 serves as the sealing element. This tube 12 is provided with an opening 13 for accommodating a thread 2. A blood vessel 8 is illustrated in FIG. 8 with the sealing device introduced therein in accordance with FIG. 7. It is apparent that the element 11, which is capable of unfolding, has been introduced into the blood vessel and that the thread 2 extends through the opening. The tube 2 is moved through the wall of the blood vessel by means of a small pipe or similar arrangement and provides sealing. For this, the opening 13 of the tube 12 and the external diameter of the fixation thread 2 are arranged in such a manner relative to one another that, on the one hand, movement is possible with respect to one another but, on the other hand, fastening of the tube is achieved. In this embodiment, tube 12 preferably consists of biologically resorbable material and has, in particular, blood clotting properties. The healing process at the opening in the blood vessel 8 is promoted in this way.

Figure 9:
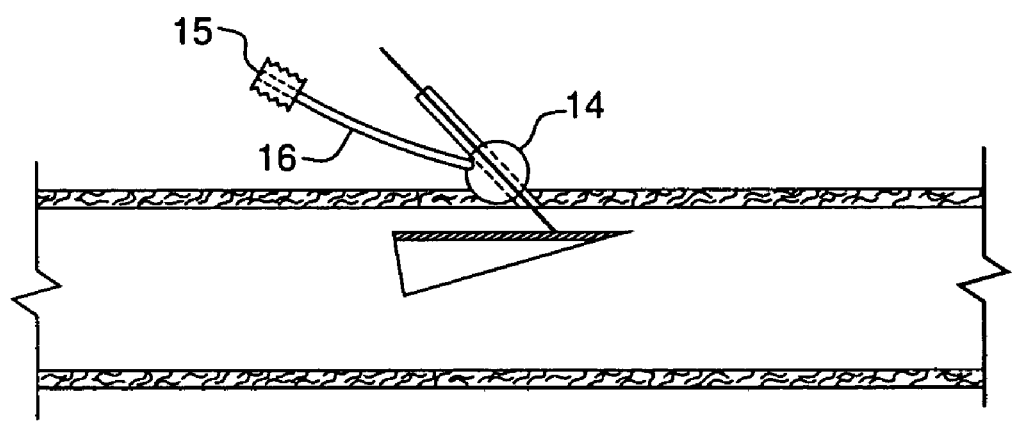
FIG. 9 shows a further embodiment of the sealing device in accordance with the invention.

FIG. 9 illustrates a further embodiment of the sealing element in a blood vessel 8 in accordance with the invention. In this way, use can be made of the element 11 which is capable of unfolding that was shown by means of FIG. 7. Here, however, an inflatable balloon 14 is positioned over the fixation thread 2 instead of the tube 12. Such positioning (of the balloon) can also take place by means of a small pipe or similar arrangement. After moving the balloon 14 downward as far as is possible, it is inflated (via line 16) by means of an inflation device 15, which is merely depicted schematically, whereby sealing of the opening in the blood vessel 8 occurs on the one hand, and a more complete clamping of the balloon 14 onto the thread 2 is produced on the other hand.

It is understood that the embodiments described above are merely examples and that the invention is not limited to these examples. Thus the fixation attachment can comprise all agents and means known in the prior art and is not limited to the thread illustrated in the drawings. In addition, the element which is capable of unfolding that is to be introduced into the blood vessel can comprise all configurations which can possibly be imagined.

The invention is also concerned with the use of bioresorbable material for the manufacture of a sealing device for the closure of puncture holes in blood vessels as described above.

The superb action/properties of the sealing device in accordance with the invention will be illustrated by means of the results of in vitro and in vivo tests which are described below.

In-Vitro Tests

Goal to test the occluder with regard to:
1. the strength of the joint between the fixation thread and the plug, directly after insertion and after 1 hour;
2. The pressure resistance of the occluder, directly and after 1 hour;
3. "freedom from leakage of blood", directly and after 1 hour;
4. its effectiveness during movement;
5. its effectiveness at various diameters of the opening;
6. the unfolding of the plug;
7. the liquid flow pattern and pressure reduction zones around the occluder (turbulence);
8. the frequency of embolization;
in order to provide a measure for the degree of effectiveness of the occluder, the occlusion frequency is determined as a function of insertion frequency, (i.e., the ratio of the number of effective occlusions to the number of times the occluder is inserted).

Test arrangements

All tests are carried out using fresh, heparin treated blood. The following parameters are known for the blood which is used:
the hemoglobin concentration (Hb);
the hematocrit value (Ht);
the concentration of thrombocytes;
the thrombo-test value (TT);
the cephalin time.

Test arrangement for tests 1 through 5

The central feature of the test arrangement is an artery of a test animal (dog, pig) with a diameter of approximately 7 mm. This is sealed at both ends—at one end by means of a clip and at the other end by means of a tap. The lumen of the artery is joined, via this tap, to a sachet of blood which is placed in a pressure bag. The pressure in the blood vessel is kept constant at 150 mm Hg. A sheath with an internal diameter of 9 French (2.9 mm) is inserted into the artery using conventional techniques. The maximum diameter of the plug has the standard value of 4.0 mm.

The insertion module is made in such a way that it can be inserted through a standard sheath with an internal diameter of 5 French (1.65 mm).

The following investigations are carried out using this test arrangement.

1. The strength of the joint between the fixation thread and the plug, directly after insertion and after 1 hour.

| | |
|---|---|
| Goal: | to test the strength of the fixation thread, the connection between the fixation thread and the plug and the deformability of the plug under the influence of a force exerted from the outside. |
| Method: | this test is carried out by hanging a weight of 250 grams onto the fixation thread for a period of 15 minutes. |

2. The pressure resistance of the occluder, directly and after 1 hour.

| | |
|---|---|
| Goal: | to test the mechanical strength and deformability of the plug under the influence of a force exerted from the inside. |
| Method: | this test is carried out by increasing the pressure in the blood vessel to 300 mm Hg for a period of 15 minutes. |

3. "Freedom from leakage of blood", directly and after 1 hour.

| | |
|---|---|
| Goal: | to examine the quantity of blood which seeps through the plug placed in the opening even though the plug is positioned properly from a mechanical point of view. |
| Method: | this measurement is combined with test 2. The quantity of blood which diffuses through the plug is measured by collecting the blood on dry pieces of gauze and weighing the pieces of gauze before and after the experiment. The difference in weight in grams is taken to be the quantity of blood, in ml, which has diffused. |

4. The effectiveness of the occluder during movement.

| | |
|---|---|
| Goal: | to test the stability of the plug during movements of the blood vessel. |
| Method: | the blood vessel is fixed at one end and an oscillating bar is hung at the other end. This bar is moved by an electric motor with a frequency of 1 Hz. A small bar is placed transversely across the blood vessel at a distance of about 2 cm from the site of the puncture in such a way that it acts as a site at which the blood vessel is hinged. The positioning of the blood vessel is such that the part connected to the bar describes the segment of a circle between 0 and 150 degrees. The puncture site is located in the moving part of the blood vessel. The duration of the test is 30 minutes. |

5. The effectiveness of the occluder at various diameters of the puncture opening.

| | |
|---|---|
| Goal: | to test the effectiveness of the occluder at various diameters of the puncture opening. |

-continued

Method: standard plugs with a cross section of 4 mm are inserted after puncture sites have been generated using the following internal sheath diameters: 5 French (1.65 mm), 7 French (2.3 mm) and 9 French (2.9 mm). These tests take place under standard conditions and are evaluated in terms of the ratio of occlusions/insertions
(O/I ratio: 100% success = 1.0; 0% success = 0).

Test arrangement for tests 6 through 8

The central feature of the test arrangement is an artery derived from a test animal (dog, pig) with a cross section of about 7 mm. The arrangement also comprises a peristaltic pump, a heat exchanger, a pressure vessel, a hemofilter and a collection vessel. The blood is pumped from the collection vessel (i.e., at atmospheric pressure) through the peristaltic pump to the pressure vessel. The pressure vessel is partly filled with air. The liquid can be held under pressure by means of a valve, which can be regulated, that is located at the top of the pressure vessel. Air bubbles which are also possible pumped out of the collection vessel can be caught and trapped in the pressure vessel. The blood flows from the pressure vessel to the artery via a heat exchanger. Two pressure lines are introduced into the artery (before and after the plug) together with a junction point for measuring temperatures. A hemofilter and a resistor which can be regulated are located behind the vessel. The temperature is held at 37° C. during the experiment and the pressure in front of the plug is held at 150 mm Hg. Using a measuring cylinder and a stop watch, the flow rate can be measured after passage of the blood through the hemofilter located behind the blood vessel, beyond the resistor, before the blood flows back into the collection vessel.

If necessary, the blood vessel can be supported on the outside by means of a (plastic) tube in order to simulate the pressure of tissues. The site for the puncture opening is thus left accessible. Use can be made of a standard, color Doppler Echo apparatus for the evaluation of flow rates and flow patterns.

The following experiments are carried out using this test arrangement.

6. The unfolding of the plug.

Goal: to test whether the plug unfolds in accordance with expectations.
Method: attempts are made to render the plug visible by means of echography and to establish its shape.

7. The liquid flow pattern and pressure reduction zones around the occluder (turbulence).

Goal: to check that the plug does not cause stenosis.
Method: the plug is inserted after the initial measurements of pressure and flow have been made. After insertion of the plug, these measurements are repeated in order to check whether the plug causes stenoses. In addition, the flow pattern around the plug is made visible by means of the color Doppler Echo technique.

8. The frequency of embolization.

Goal: to check that the plug does not act as a source of embolization.
Method: each time a plug is inserted, blood is allowed to circulate for a period of 2 hours. After this time, the hemofilter is checked and renewed. The pores of the hemofilter are the same in size as those of filters used during extracorporeal circulation. The number, size and (if possible) composition of the emboli are recorded.

Tests 6, 7 and 8 can be carried out simultaneously. Tests 6 and 7 are carried out both at the beginning of the investigations and just before the end of the tests.

In Vivo Tests

The following aspects are of importance in in vivo tests.
the stability of the plug;
the frequency at which bleeding occurs at the location of the puncture site;
the effect of rapid mobilization (of the patient) on the stability of the plug;
the healing of the wall of the blood vessel at the location of the puncture site;
the formation of aneurysms at the location of the puncture site;
the frequency at which stenoses of the blood vessels occur at the location of the plug;
the resorption of the plug and the fixation thread as a function of time;
scar formation around the plug and the fixation thread;
the thrombogenetic action of the plug;
the frequency of embolization caused by the material of the plug;
the occurrence of infections at the location of the plug site;
the toxicity of the plug and the fixation thread.

Any animal of adequate size can serve as the test animal (dog, pig). After adequate anesthesia and respiratory connection, a catheter is introduced into the a. carotis in order to record pressure. The process of treating with heparin takes place by intravenously administering 100 U/kg of body weight. Blood samples are taken for the determination of hemoglobin (Hb), the hemocrit value (Ht), thrombocytes, thrombo-test (TT) values and the cephalin time.

A blood vessel of adequate diameter is now located (a. iliaca, aorta). An initial angiogram of the blood vessel which is to be punctured is recorded by means of a catheter in the a. carotis. A standard 9 French sheath is inserted followed by the insertion of a standard plug (diameter 4 mm).

One or more puncture sites can be used depending on the size of the blood vessel which has been selected. After inserting the plug, checks are made over a period of 15 minutes as to whether the plug remains stable at its location and whether or not there is "oozing" at the location of the puncture site (this evaluation is semi-quantitative). After the procedure, a check angiograph is made of the punctured segment of the blood vessel before removing the sheath from the a. carotis. In the event of survival (of the test animal), blood samples are taken the following day for the determination of Hb and Ht. In addition, a clinical examination is made for signs of emboli. A check angiograph is made of the punctured segment of the blood vessel before termination. After termination, the puncture site is located, removed and fixed in formalin (for optical microscopy) or glutaraldehyde (for scanning electron microscopy, SEM). Survival periods (are selected to be): 0, 1, 7, 30, 90 and 180 days.

A control group consists of test animals which have undergone the same procedure except for the arterial puncture.

The results of both in vivo and in vitro tests show that the sealing device in accordance with the invention is superbly well suited for the application envisaged.

We claim:

1. An assembly for introduction into an incision and for sealing an opening in the wall of a blood vessel having a vessel wall with inner and outer wall surfaces and a preexisting hollow interior, said assembly comprising:
    a sheath arranged to be placed inside said incision and directed to the opening in the wall of the blood vessel;
    an occlusion element, arranged to be inserted through said sheath into and through the opening in the wall of the blood vessel for disposition within the preexisting hollow interior of the blood vessel, said occlusion element not serving to form the preexisting hollow interior of the blood vessel;
    a retaining thread having a distal section and a proximal section, said distal section being arranged to be inserted through said sheath into and through the opening in the wall of the blood vessel, said distal section being attached to said occlusion element, said proximal section being arranged to remain proximal to the opening in the blood vessel, whereupon a portion of said retaining thread bridges the wall of the blood vessel through the opening, said retaining thread being further arranged to apply force to said occlusion element to cause the engagement of said occlusion element with the inner wall surface of the blood vessel while said occlusion element remains within the preexisting hollow interior of the blood vessel; and
    a locking element, arranged to be slidably mounted on said retaining thread to apply force to the outer wall surface of the blood vessel to produce tension in said retaining thread confined to the portion of said retaining thread bridging the wall of the blood vessel.

2. The assembly of claim 1, wherein said occlusion element and said retaining thread are resorbable.

3. The assembly of claim 2 wherein said locking element is resorbable.

4. An assembly for introduction into an incision and for sealing an opening in the wall of a blood vessel having a vessel wall with inner and outer wall surfaces and a preexisting hollow interior, said assembly comprising;
    a sheath arranged to be placed inside said incision and directed to the opening in the wall of the blood vessel;
    a first resorbable segment having a distal section and a proximal section, said distal section being arranged to be inserted through said sheath into and through the opening in the wall of the blood vessel;
    a second resorbable segment attached to said distal section of said first resorbable segment and arranged to be inserted through said sheath into and through the opening in the wall of the blood vessel for disposition within the preexisting hollow interior of the blood vessel, said second resorbable segment not serving to form the preexisting hollow interior of the blood vessel, said proximal section of said first resorbable segment being arranged to remain proximal to the opening in the wall of the blood vessel, whereupon a portion of said first resorbable segment bridges the wall of the blood vessel through the opening, said first resorbable segment being further arranged to apply force to said second resorbable segment to cause the engagement of said second resorbable segment with the inner wall surface of the blood vessel while said second resorbable segment is within the preexisting hollow interior of the blood vessel;
    a third resorbable segment arranged to be slidably mounted on said first resorbable segment to apply force to the outer wall surface of the blood vessel to produce tension in said first resorbable segment confined to the portion of said first resorbable segment bridging the wall of the blood vessel.

5. The assembly of claim 4, wherein said second resorbable segment comprises an occlusion element which causes the sealing of said opening.

6. The assembly of claim 4, wherein said second resorbable segment comprises a spreadable element which causes the sealing of said opening.

7. An assembly for introduction into an incision and for sealing an opening in the wall of a blood vessel having a vessel wall with inner and outer wall surfaces and a preexisting hollow interior, the wall having a wall thickness between the inner and outer wall surfaces, said assembly comprising;
    a first member arranged to be placed inside the incision and directed to the opening in the wall of the blood vessel;
    an occlusion element, arranged to be inserted through said first member into and through the opening in the wall of the blood vessel for disposition within the preexisting hollow interior of the blood vessel, said occlusion element not serving to form the preexisting hollow interior of the blood vessel;
    a retaining thread having a distal section and a proximal section, said distal section being arranged to be inserted through the first member into the opening in the wall of the blood vessel, said distal section being attached to said occlusion element, said proximal section being arranged to remain proximal to the opening in the blood vessel, whereupon a portion of said retaining thread bridges the wall thickness through the opening, with said retaining thread being further arranged to apply force to said occlusion element to cause the engagement of said occlusion element with the inner wall surface of the blood vessel while said occlusion element remains within the preexisting hollow interior of the blood vessel; and
    a locking element arranged to be slidably mounted on said retaining thread to apply force to the outer wall surface of the blood vessel to produce tension in said retaining thread confined to the portion of said retaining thread bridging the wall thickness of the blood vessel.

8. The assembly of claim 7, wherein said occlusion element and said retaining thread are resorbable.

9. The assembly of claim 8 wherein said locking element is resorbable.

10. A bioabsorbable occlusion assembly for introduction into an incision and for sealing an opening in the wall of a blood vessel having a vessel wall with inner and outer wall surfaces, the blood vessel being located beneath the skin, said assembly comprising;
    an occlusion element which is changeable in shape and sized to be fitted through the opening in the wall of the blood vessel and thereafter to lie generally adjacent to the inner wall surface during use;
    a retaining thread sized for reception in the incision and in operative connection with said occlusion element to extend proximally of the occlusion element through the incision; and
    a locking element separate from said occlusion element and sized to be received in the incision and beneath the skin and operatively connected to and maintaining tension upon said retaining thread to retain the wall of the blood vessel between said locking element and said occlusion element during use.

11. The assembly of claim 10, wherein said occlusion element is spreadable.

12. A sealing device for percutaneously sealing a percutaneously made puncture in a blood vessel having a vessel wall with inner and outer wall surfaces, said sealing device comprising
an occlusion element which is changeable in shape and constructed and arranged to be percutaneously inserted into the blood vessel, whereupon it changes shape;
a retaining thread connected to the occlusion element, said occlusion element being repositionable after insertion into the blood vessel to engage against the inner wall surface; and
a locking element constructed and arranged to be inserted percutaneously and be moved over the retaining thread exterior to and adjacent the outer wall surface of the blood vessel and into cooperative relation with said occlusion element while said occlusion element remains within the preexisting hollow interior of the blood vessel to thereby seal the puncture in the blood vessel.

13. A method of sealing an incision and an opening in a blood vessel having a preexisting hollow interior and a vessel wall with inner and outer wall surfaces creating a wall thickness between the surfaces, wherein the incision extends through the skin of a patient, and wherein the opening comprises a percutaneously made puncture in the blood vessel, said method comprising the steps of:
supplying an occlusion system comprising a first member, a first resorbable segment, a second resorbable segment, and a third resorbable segment, said first resorbable segment comprising a distal section and a proximal section, said distal section being operatively coupled to said second resorbable segment, said proximal section being arranged to remain proximal to the opening in the blood vessel;
inserting said first member into said incision and directed to the opening in the wall of the blood vessel;
inserting said first resorbable segment and said second resorbable segment through said first member into and through the opening in the wall of the blood vessel so that said second resorbable segment is located in the preexisting hollow interior of the blood vessel, said second resorbable segment not serving to form the preexisting hollow interior of the blood vessel;
applying a force on said proximal section of said first resorbable segment while said second resorbable segment remains within the preexisting hollow interior of the blood vessel, said force applied on said proximal section causing the engagement of said second resorbable segment with the inner wall surface of the blood vessel, whereupon a portion of said first resorbable segment bridges the wall thickness; and
sliding said third resorbable segment along said first resorbable segment to apply force to the outer wall surface of the blood vessel to produce tension in said first resorbable segment confined to the portion of said first resorbable segment bridging the wall thickness of the blood vessel.

14. The method of claim 13, wherein said second resorbable segment comprises an occlusion element which causes the sealing of the opening.

15. The method of claim 13, wherein said second resorbable segment comprises a spreadable element which causes the sealing of the opening.

16. The method claim 13, wherein said first member comprises a sheath.

17. A method of sealing an incision and an opening in a blood vessel, wherein the incision extends through the skin of a patient, and wherein the opening comprises a percutaneously made puncture in the blood vessel, the blood vessel having a preexisting hollow interior and a vessel wall with inner and outer wall surfaces creating a wall thickness between the surfaces, said method comprising the steps of:
supplying an occlusion system comprising a first member, a first resorbable segment, a second resorbable segment, and a third resorbable segment, said first resorbable segment comprising a distal section and a proximal section, said distal section being operatively coupled to said second resorbable segment, said proximal section being arranged to remain proximal to the opening in the blood vessel;
inserting said first member into said incision and directed to the opening in the wall of the blood vessel, wherein the insertion of said first member causes the insertion of said first resorbable segment and said second resorbable segment into and through the opening in the wall of the blood vessel so that said second resorbable segment is located in the preexisting hollow interior of the blood vessel, said second resorbable segment not serving to form the preexisting hollow interior of the blood vessel;
applying a force on said proximal section of said first resorbable segment while said second resorbable segment remains within the preexisting hollow interior of the blood vessel, said force causing the engagement of said second resorbable segment with the inner wall surface of the blood vessel, whereupon a portion of said first resorbable segment bridges the wall thickness; and
sliding said third resorbable segment along said first resorbable segment to apply force to the outer wall surface of the blood vessel to produce tension in said first resorbable segment confined to the portion of said first resorbable segment bridging the wall thickness of the blood vessel.

18. The method of claim 17, wherein said second resorbable segment comprises an occlusion element which causes the sealing of the opening.

19. The method of claim 17, wherein said second resorbable segment comprises a spreadable element which causes the sealing of the opening.

20. The method of claim 17, wherein said first member comprises a sheath.

21. In combining of a blood vessel of a living being and a closure assembly, said blood vessel having a vessel wall with inner and outer wall surfaces and a preexisting hollow interior, said blood vessel including an opening in said vessel wall, said assembly being arranged to be inserted through an incision in the living being to seal said opening in said blood vessel wall and comprising:
a sheath arranged to be placed inside said incision and directed to the opening in said wall of said blood vessel;
an occlusion element, arranged to be inserted through said sheath into and through said opening in said wall of said blood vessel for disposition within said preexisting hollow interior of said blood vessel, said occlusion element not serving to form said preexisting hollow interior of said blood vessel;
a retaining thread having a distal section and a proximal section, said distal section being arranged to be inserted through said sheath into and through said opening in said wall of said blood vessel, said distal section being attached to said occlusion element, said proximal section being arranged to remain proximal to said opening in said blood vessel, whereupon a portion of said retaining thread bridges said wall of said blood vessel through said opening, said retaining thread being further arranged to apply force to said occlusion element to cause said engagement of said occlusion element with said inner wall surface of said blood vessel while said occlusion element remains within said preexisting hollow interior of said blood vessel; and a locking element, arranged to be slidably mounted on said retaining thread to apply force to said outer wall surface of said blood vessel to produce tension in said retaining thread confined to said portion of said retaining thread bridging said wall of said blood vessel.

22. In combining of a blood vessel of a living being and a closure assembly, said blood vessel having a vessel wall with inner and outer wall surfaces and a preexisting hollow interior, said blood vessel including an opening in said vessel wall, said assembly being arranged to be inserted through an incision in the living being to seal said opening in said blood vessel wall and comprising:

a sheath arranged to be placed inside said incision and directed to said opening in said wall of said blood vessel;

a first resorbable segment having a distal section and a proximal section, said distal section being arranged to be inserted through said sheath into and through said opening in said wall of said blood vessel;

a second resorbable segment attached to said distal section of said first resorbable section and arranged to be inserted through said sheath into and through said opening in said wall of said blood vessel for disposition within said preexisting hollow interior of said blood vessel, said second resorbable segment not serving to form said preexisting hollow interior of said blood vessel, said proximal section of said first resorbable segment being arranged to remain proximal to said opening in said wall of said blood vessel, whereupon a portion of said first resorbable segment bridges said wall of said blood vessel through said opening, said first resorbable segment being further arranged to apply force to said second resorbable segment to cause the engagement of said second resorbable segment with said inner wall surface of said blood vessel while said second resorbable segment is within said preexisting hollow interior of said blood vessel;

a third resorbable segment arranged to be slidably mounted on said first resorbable segment to apply force to said outer wall surface of said blood vessel to produce tension in said first resorbable segment confined to said portion of said first resorbable segment bridging said wall of said blood vessel.

23. In combining of a blood vessel of a living being and a closure assembly, said blood vessel having a vessel wall with inner and outer wall surfaces and a preexisting hollow interior, said blood vessel including an opening in said vessel wall, said assembly being arranged to be inserted through an incision in the living being to seal said opening in said blood vessel wall and comprising:

a first member arranged to be placed inside said incision and directed to said opening in said wall of said blood vessel;

an occlusion element, arranged to be inserted through said first member into and through said opening in said wall of said blood vessel for disposition within said preexisting hollow interior of said blood vessel, said occlusion element not serving to form said preexisting hollow interior of said blood vessel;

a retaining thread having a distal section and a proximal section, said distal section being arranged to be inserted through said first member into said opening in said wall of said blood vessel, said distal section being attached to said occlusion element, said proximal section being arranged to remain proximal to said opening in said blood vessel, whereupon a portion of said retaining thread bridges said wall thickness through said opening, with said retaining thread being further arranged to apply force to said occlusion element to cause said engagement of said occlusion element with said inner wall surface of said blood vessel while said occlusion element remains within said preexisting hollow interior of said blood vessel; and a locking element arranged to be slidably mounted on said retaining thread to apply force to said outer wall surface of said blood vessel to produce tension in said retaining thread confined to said portion of said retaining thread bridging said wall thickness of said blood vessel.

24. In combining of a blood vessel of a living being and a closure assembly, said blood vessel having a vessel wall with inner and outer wall surfaces and a preexisting hollow interior, said blood vessel including an opening in said vessel wall, said assembly being arranged to be inserted through an incision in the living being to seal said opening in said blood vessel wall and comprising:

an occlusion element which is changeable in shape and constructed and arranged to be percutaneously inserted into said blood vessel for disposition within said preexisting hollow interior of said blood vessel, said occlusion element not serving to form said preexisting hollow interior of said blood vessel, whereupon it changes shape;

a retaining thread connected to said occlusion element, said occlusion element being repositionable after insertion into said blood vessel to engage against said inner wall surface; and a locking element constructed and arranged to be inserted percutaneously and be moved over said retaining thread exterior to and adjacent said outer wall surface of said blood vessel and into cooperative relation with said occlusion element while said occlusion element remains within said preexisting hollow interior of said blood vessel to thereby seal said puncture in said blood vessel.

* * * * *